US005525349A

United States Patent [19]
Robertson et al.

[11] Patent Number: 5,525,349
[45] Date of Patent: * Jun. 11, 1996

[54] COMPOSITIONS AND METHODS FOR TREATING THE CORNEA INCONJUNCTION WITH LASER IRRADIATION

[75] Inventors: Stella M. Robertson, Arlington; Herman M. Kunkle, Jr., Mansfield, both of Tex.

[73] Assignee: Alcon Laboratories, Inc., Fort Worth, Tex.

[*] Notice: The portion of the term of this patent subsequent to Oct. 3, 2008, has been disclaimed.

[21] Appl. No.: 332,688

[22] Filed: Nov. 1, 1994

Related U.S. Application Data

[63] Continuation of Ser. No. 279,661, Jul. 25, 1994, Pat. No. 5,401,509, which is a continuation of Ser. No. 220,780, Mar. 31, 1994, abandoned, which is a continuation of Ser. No. 101,862, Aug. 4, 1993, Pat. No. 5,360,611, which is a continuation of Ser. No. 866,730, Apr. 10, 1992, Pat. No. 5,271,939, which is a continuation of Ser. No. 531,179, May 31, 1990, Pat. No. 5,124,392, which is a continuation-in-part of Ser. No. 253,009, Oct. 3, 1988, Pat. No. 4,939,135.

[51] Int. Cl.$^6$ ............................................. A61K 31/56
[52] U.S. Cl. .................... 424/427; 514/39; 514/169; 514/177; 514/178; 514/179; 514/180; 514/314
[58] Field of Search .................... 424/427; 514/169, 514/177, 178, 179, 180, 314, 39, 40

[56] References Cited

U.S. PATENT DOCUMENTS

| | | |
|---|---|---|
| 4,436,745 | 3/1984 | York, Jr. .................... 424/273 |
| 4,438,272 | 3/1984 | York, Jr. .................... 548/308 |
| 4,454,151 | 6/1984 | Waterbury .................... 424/274 |
| 4,474,751 | 10/1984 | Haslam et al. ................ 514/11 |
| 4,559,343 | 12/1985 | Han et al. .................... 514/264 |
| 4,599,353 | 7/1986 | Bito .......................... 514/278 |
| 4,600,717 | 7/1986 | York, Jr. .................... 514/278 |
| 4,665,913 | 5/1987 | L'Esperance, Jr. ............ 128/303.1 |
| 4,686,214 | 8/1987 | Boltralik .................... 514/179 |
| 4,692,460 | 9/1987 | Carson ....................... 514/443 |
| 4,717,725 | 1/1988 | York, Jr. .................... 514/278 |
| 4,717,727 | 1/1988 | Günzler et al. ............... 514/354 |
| 4,732,148 | 3/1988 | L'Esperance, Jr. ............ 128/303.1 |
| 4,797,422 | 1/1989 | Testa ......................... 514/646 |
| 4,939,135 | 7/1990 | Robertson .................... 514/179 |
| 4,966,911 | 10/1990 | Clark et al. ................. 514/385 |
| 5,036,056 | 7/1991 | Kludas ....................... 514/54 |
| 5,098,896 | 3/1992 | Muller ....................... 514/724 |
| 5,124,392 | 6/1992 | Robertson .................... 424/427 |
| 5,149,693 | 9/1992 | Cagle et al. ................. 514/40 |
| 5,149,694 | 9/1992 | Cagle et al. ................. 514/40 |

FOREIGN PATENT DOCUMENTS

| | | |
|---|---|---|
| 0140998 | 11/1983 | European Pat. Off. . |
| 0189272 | 1/1986 | European Pat. Off. . |
| 0190018 | 1/1986 | European Pat. Off. . |
| 2144993A | 8/1984 | United Kingdom . |
| 8602271 | 4/1986 | WIPO . |

OTHER PUBLICATIONS

Taboada et al., *Health Physics*, vol. 40, pp. 677–683 (May 1981) "Response of the Corneal Epithelium to KrFExcimer Laser Pulses".

Del Pero et al., *Human Excimer Laser Lamellar Refractive Keratectomy—A Clinical Study*, ARVO Annual Meeting Abstract Issue, p. 281, No. 8 (1988).

Gaster et al., *Excimer Laser Ablation and Wound Healing of Superficial Cornea in Rabbits and Primates*, ARVO Annual Meeting Abstract Issue, p. 309, No. 4 (1988).

Tuft et al., *Corneal Remodelling Following Anterior Keratectomy*, ARVO Annual Meeting Abstract Issue, p. 310, No. 7 (1988).

Olsen et al., "The Effect of Steroids on the Healing of the Corneal Endothelim," *Acta Ophthalmologica*, 62, pp. 893–899 (1984).

Singh, "Corticosteroids in Corneal Endothelial Wound Healing," *Annals of Ophthalmology*, vol. 17, No. 4, pp. 238–243 (Apr. 1985).

Woost et al., "Effect of Growth Factors with Dexamethasone on Healing of Rabbit Corneal Stromal Incisions," *Exp. Eye Res.*, 40, pp. 47–60 (1985).

Kössendrup et al., "Influence of Cyclosporin A, Dexamethasone, and Benzalkonium Chloride (BAK) on Corneal Epithelial Wound Healing in the Rabbit and Guinea Pig Eye," *Cornea*, 4, pp. 177–181 (1985/1986).

Sanchez et al., "Effect of Topical Steroids on the Healing of the Corneal Endothelim," *Inves. Ophth.*, vol. 13, pp. 17–22 (Dec. 1974).

Barrandon et al., "Cell Migration Is Essential for Sustained Growth of Keratinocyte Colonies: The Roles of Transforming Growth Factor-$\alpha$ and Epidermal Growth Factor" *Cell*, vol. 50, pp. 1131–1137 (Sep. 25, 1987), Lawrence et al., The Reversal of an Adriamycin© Induced Healing Impairment with Chemoattractants and Growth Factors *Annal. Surg.* 203, pp. 142–147 (1986).

Fujikawa et al., "Fibronectin in Healing Rabbit Corneal Wounds", *Laboratory Investigation*, vol. 45, No. 2, pp. 120–128 (1981).

Ohashi et al., "Aldose Reductase Inhibitor (CT–112) Eyedrops for Diabetic Corneal Epitheliopathy," *American Journal of Ophthalmology*, vol. 105, No. 3 (Mar. 1988).

(List continued on next page.)

Primary Examiner—Gollamudi S. Kishore
Attorney, Agent, or Firm—Jeffrey S. Schira; Sally Yeager

[57] ABSTRACT

Methods for preventing and treating corneal haze resulting from exposure of the eye to laser irradiation are disclosed. The methods include administration of compositions of wound healing modulators to the eye. Compositions for use in preventing and treating the corneal haze are also disclosed.

13 Claims, No Drawings

OTHER PUBLICATIONS

Fisher, "Intracellular Production of Oxygen–Derived Free Radicals," *Proceedings of a Book Lodge Symposium*, Apr. 1987.

Meister, "Selective Modification of Glutathione Metabolism," *Science*, vol. 220, pp. 472–477, (Apr. 1988).

Phan et al., "Regulation of Macrophage–Derived Fibroblast Growth Factor Release by Arachidonate Metabolites," *Journal of Leukocyte Biology*, 42: 106–113 (1987).

L'Esperance, Jr. et al., "Human Excimer Laser Keratectomy: Short Term Histopathology," *Journal of Refractive Surgery*, vol. 4, No. 4, pp. 118–124 (Jul./Aug. 1988).

Maxidex® product information, *Physicians' Desk Reference for Ophthalmology*, pp. 81–82 (1989).

COMPOSITIONS AND METHODS FOR TREATING THE CORNEA INCONJUNCTION WITH LASER IRRADIATION

This is a continuation of U.S. patent application Ser. No. 08/279,661, filed Jul. 25, 1994, now U.S. Pat. No. 5,401,509, which is a continuation of Ser. No. 08/220,780, filed Mar. 31, 1994, now abandoned, which is a continuation of U.S. Ser. No. 08/101,862, filed on Aug. 4, 1993, now U.S. Pat. No. 5,360,611, which is a continuation of U.S. patent application Ser. No. 07/866,730, filed Apr. 10, 1992, now U.S. Pat. No. 5,271,939, which is a continuation of U.S. patent application Ser. No. 07/531,179, filed May 31, 1990, now U.S. Pat. No. 5,124,392, which is a continuation in part of U.S. patent application Ser. No. 07/253,009, filed Oct. 3, 1988, now U.S. Pat. No. 4,939,135.

BACKGROUND OF THE INVENTION

1. Field of the Invention

This invention relates to methods of treatment and pharmaceutical compositions used for the prevention and treatment of corneal haze. The formation of corneal haze as an artifact resulting from exposure of the cornea to laser irradiation is a new phenomenon. The methods of the present invention for the prevention and treatment of corneal haze involve the application of compositions to the eye prior to, during and after irradiation.

2. Description of Related Art

Ophthalmic operations such as corneal transplants and keratotomies traditionally are performed by surgeons using cutting instruments. At the incision site the cutting edge of these instruments unavoidably damages several layers of cells on either side of the point of entry. This impairs the ability of the surgical wound to heal without resulting scar tissue. The use of lasers in ophthalmic surgery has developed partly in an effort to minimize damage to cells as a result of disturbance due to instrument incisions. Infrared lasers such as carbon dioxide ($CO_2$) lasers have been used to achieve controlled local ablation or incision of the cornea. In the past, use of $CO_2$ lasers and most lasers emitting in the visible spectrum, were known to damage or char cells adjacent to the site of ablation or incision because results are thermally achieved through photocoagulation and/or photovaporization. However, through the improvement of these lasers and techniques, it is now possible to better control the ablation or incision of the cornea, thereby eliminating or reducing the damaging results.

With respect to lasers emitting in the ultraviolet (UV) range, the radiation decomposes the molecules of tissues photochemically by directly breaking intramolecular bonds. Thus, there is not the characteristic damage to adjacent cells resulting in photothermal ablation.

The use of UV lasers, which emit radiation below about 400 nanometers (nm), and the use of improved $CO_2$ lasers and most lasers emitting in the visible spectrum, has dramatically improved the possibilities for ophthalmic surgery. For example, corneal transplants and keratotomies may be more precisely performed with less damage resulting from the procedure itself. Methods for conducting ophthalmic surgery using an ultraviolet emitting laser are described in U.S. Pat. Nos. 4,665,913 and 4,732,148 issued to L'Esperance, both of which are incorporated herein by reference to the extent that they disclose methods and devices for achieving a predetermined refractive correction by volumetric removal of corneal tissue. Removal is through the phenomenon of photoablation of the cornea namely, of the epithelium, Bowman's membrane and stroma levels of the cornea, using incident UV laser irradiation. Non UV lasers can now also be used to photoablate the cornea for achieving a predetermined refractive correction through the volumetric removal of corneal tissue.

The ophthalmic surgical methods disclosed by, for example, L'Esperance include various procedures for correcting eye disorders attributable to abnormal curvature of the cornea, collectively referred to as laser refractive keratoplasties (LRK). It has been forecast that the eventual adoption of LRK to ablate the cornea for correction of common myopic or hyperopic conditions will largely eliminate the need for eyeglasses, contact lenses or other methods of vision correction using lenses. LRK can also be used to correct astigmatisms; remove corneal scar tissue; and excise corneal tissue for accommodation of corneas in corneal transplants. In addition, LRK and other procedures involving lasers can be used to perform incisions, including incisions for refractive effects such as radial keratotomy.

Even with the improved surgical methods using UV and non UV emitting lasers, such as $CO_2$ and most lasers emitting in the visible spectrum, a condition known as "corneal haze" may result as a response to use of the laser during ophthalmic surgery. Corneal haze, as discussed herein, is an artifact which has not been observed as a result of ophthalmic surgery until the advent of use of these lasers. The artifact is seen as opacification of the cornea, which in humans is composed of an epithelial layer, Bowman's membrane, the stroma, Descemet's membrane and the endothelium. The artifact resulting from laser surgery is seen in different parts of the cornea but particularly in the stroma. When the artifact does appear it can usually only be observed by use of a slit lamp. It is not known precisely why the artifact sometimes occurs after photoablation of the cornea. The development of corneal haze is of potentially greater concern in those procedures affecting a large surface of the cornea versus procedures involving laser incisions.

A study was done on the response of the corneal epithelium to excimer lasers (lasers based on the excited state of a halogen atom combining with the ground state of a rare gas such as krypton or xenon) due to concern over use of the lasers in work environments, for example, in isotope separation, thermonuclear fusion, photochemistry and underwater communications; see Taboada, et al., *Health Physics*, Volume 40, pp. 677–683 (May, 1981). In that study rabbits were exposed to pulsed laser radiation of 248 nm. The rabbits' corneal epitheliums exhibited increasing levels of damage with increasing exposure. As a result of this damage, the authors suggested that guidelines for workers exposed to short pulse radiation be redefined.

The corneal haze or artifact to be prevented or treated according to the present invention is not a result of the use of lasers in the work area. It is rather a result of purposeful and direct exposure of the cornea to laser irradiation during ophthalmic surgery. Recent studies have been done regarding the corneal haze which results from exposure to lasers. For example, in one study, seven patients received laser corneal ablation with a 193 nm Questek excimer laser. Post ablation examination with a slit beam showed a speckled haze at the interface between the epithelium and stroma; see Del Pero, et al., *Human Excimer Laser Lamellar Refractive Keratectomy—A Clinical Study*, ARVO Annual Meeting Abstract Issue, p. 281, No. 8 (1988). In another study ablation with a 193 nm excimer laser resulted in a slight haze in the corneas of rabbits and primates. The haze was observable by slit lamp but disappeared after two weeks.

However, in the rabbits a material resembling plasma membrane was reported in Descemet's membrane, which is located between the posterior surface of the stroma and the anterior surface of the corneal endothelium; see Gaster et al., *Excimer Laser Ablation and Wound Healing of Superficial Cornea in Rabbits and Primates*, ARVO Annual Meeting Abstract Issue, p. 309, No. 4 (1988). In another study discs were formed in the corneal stromas of rabbits by excimer laser photoablation at 193 nm. A stromal haze developed by one month, but corneal transparency did improve after 6 months; see Tuft et al., *Corneal Remodeling Following Anterior Keratectomy*, ARVO Annual Meeting Abstract Issue, p. 310, No. 7 (1988).

With the improvement of lasers, particularly UV, $CO_2$, and, most lasers emitting in the visible spectrum, and their use in ophthalmic surgery, there has developed a need for prevention of the corneal haze which results during ophthalmic procedures involving the use of lasers.

It is an objective of this invention to provide methods of treatment to prevent the appearance of and/or treat corneal haze induced by laser irradiation. It is another objective of this invention to provide compositions for treating eyes before, during or after exposure to a laser which will prevent and/or treat corneal haze.

SUMMARY OF THE INVENTION

Corneal haze is an artifact which may result from the photoablation of the cornea during ophthalmic surgery conducted, for example, according to the methods described by L'Esperance in U.S. Pat. Nos. 4,665,913 and 4,732,148. As defined herein, corneal haze presents a new problem as it has not been observed as a result of ophthalmic surgery until the use of lasers to sculpt the cornea to achieve a predetermined configuration as a result of photoablation.

According to the present invention, compositions containing agents which modulate wound healing are used for the prevention and treatment of corneal haze. Agents which can be used in the compositions, alone or in combination with other such agents, include: steroids, growth factors, basement membrane components, anti-oxidants, regulators of collagen structure, aldose reductase inhibitors, nonsteroidal antiinflammatories, immunomodulators, antiallergics, fatty acid derivatives which are products of the arachidonic acid cascade and antimicrobials.

The compositions containing the wound healing modulators are formulated as solutions, suspensions, emulsions or gels depending on the characteristics of the wound healing modulator. The compositions can also be delivered via use of a collagen shield, contact lenses or other solid matrixes capable of delivering drugs to the cornea placed on the ocular surface.

The compositions are used to prevent or treat corneal haze and are applied to the eye prior to and/or during surgical exposure to laser radiation and/or postoperatively.

DETAILED DESCRIPTION OF PREFERRED EMBODIMENTS

The present invention is directed to methods of treatment of corneal haze resulting from laser irradiation of the eye. The invention also encompasses compositions which contain agents that modulate wound healing, said agents referred to herein as "wound healing modulators." For purposes of the present specification of the term "wound healing modulator" is used to identify compounds or compositions that facilitate the prevention or reduction of corneal haze as that term is used herein, regardless of any theoretical explanation for its development. For purposes herein the term "corneal haze" refers to the clouding of the cornea which results from exposure of the cornea to laser radiation during eye surgery. The compositions containing the wound healing modulators are useful for prevention and treatment of corneal haze which results from surgical exposure to laser radiation. In particular the compositions are useful for the prevention and treatment of corneal haze resulting from LRK.

Wound healing modulators, included alone or in combinations in the compositions of the present invention, include: steroids, growth factors, basement membrane components, anti-oxidants, regulators of collagen structure, aldose reductase inhibitors (ARIs) nonsteroidal antiinflammatories (NSAIs), immunomodulators, antiallergics, fatty acid derivatives, which are products of the arachidonic acid cascade and antimicrobials. All of the wound healing modulators disclosed herein are known. However, none are known or disclosed, alone or in combinations, for the prevention of corneal haze resulting from exposure to laser radiation during ophthalmic surgery.

Without intending to be bound by any theory as to why corneal haze may appear, it is believed that one or more of the following events may be occurring. First, it is believed the corneal haze is a scar resulting from actual wound repair taking place after photoablation of the cornea. Second, it is thought that the fibroblasts of the stroma may be improperly activated in response to the laser. Third, the radiation emitted by the laser may damage collagen fibrils resulting in their improper alignment. Fourth, the laser may kill or damage fibroblasts in the stroma. Fifth, the corneal haze may result from corneal edema which occurs following photoablation.

With respect to the first theory, the scar, however subtle, may result from wound repair taking place after photoablation. It may arise due to, for example, improper collagen repair, improper epithelial cell coverage of the cornea, or inflammation.

To prevent or reduce scar formation due to improper collagen repair the following wound healing modulators can be used: steroids, growth factors, basement membrane components and regulators of collagen structure.

Steroids are known for their role in controlling inflammation and inhibiting wound healing; see, Olsen et al., *The Effect of Steroids on the Healing of the Corneal Endothelium*, Acta Ophthalmologica, 62, pp. 893–899 (1984); Singh, *Corticosteroids in Corneal Endothelial Wound Healing*, Annals of Ophthalmology, Vol. 17, no. 4, pp. 238–243 (April, 1985); Woost et al., *Effect of Growth Factors with Dexamethasone on Healing of Rabbit Corneal Stromal Incisions*, Exp. Eye Res., 40, pp. 47–60 (1985); Kossendrup et al., *Influence of Cyclosporin A. Dexamethasone, and Benzalkonium Chloride (BAC) on Corneal Epithelial Wound Healing in the Rabbit and Guinea Pig Eye*, Cornea, 4, pp. 177–181 (1985/1986), the contents of all of which are incorporated herein by reference. The positive effect of the delay in wound healing is alleviation or prevention of scar formation possibly due to regulation of the pattern of healing; see for example, Sanchez, et al., *Effect of Topical Steroids on the Healing of the Corneal Endothelium*, Inves. Ophth., Vol 13, pp. 17–22 (December 1974), the contents of which are incorporated herein by reference.

The steroids which can be used according to the present invention include all steroids which are capable of preventing or treating corneal haze resulting from laser irradiation. This includes corticosteroids, preferably glucocorticoids, and all derivatives and isomers thereof. For example, steroids which can be employed in the present invention to prevent and treat corneal haze include: dexamethasone; fluorometholone; medrysone; betamethasone; triamcinolone; prednisone; prednisolone, such as prednisolone acetate; hydrocortisone and pharmaceutically acceptable salts thereof; prednicarbate; deflazacort; halomethasone; tixolcortol; prednylidene (21 diethylaminoacetate); prednival; paramethasone; methylprednisolone; meprednisone; mazipredone; isoflupredone; halopredone acetate; halcinonide; formocortal; flurandrenolide; fluprednisolone; fluprednidine acetate; fluperolone acetate; fluocortolone; fluocortin butyl; fluocinonide; fluocinolone acetonide; flunisolide; flumethasone; fludrocortisone; fluclorinide; enoxolone; difluprednate; diflucortolone; diflorasone diacetate; desoximetasone (desoxymethasone); desonide; descinolone; cortivazol; corticosterone; cortisone; cloprednol; clocortolone; clobetasone; clobetasol; chloroprednisone; cafestol; budesonide; beclomethasone; amcinonide; allopregnane acetonide; alclometasone; 21 acetoxypregnenolone; tralonide; diflorasone acetate; deacylcortivazol; budesonide and deacylcortivazol oxetanone. The above-cited steroids are known compounds. Further information regarding the compounds can be found in *The Merck Index* Tenth Edition, 1983, and the publications cited therein, the entire contents of which are incorporated herein by reference. Additional examples of steroids which can be used according to the present invention include: dexamethasone ether derivatives, which are the subject matter of the commonly assigned patent application Ser. No. 922,810, the entire contents of which are incorporated herein by reference; alkyloid steroids of the pregnane series (Rimexolone) disclosed generally in U.S. Pat. No. 3,947,478 issued Mar. 30, 1976, and specifically for ophthalmic use in U.S. Pat. No. 4,686,214 issued Aug. 11, 1987, the entire contents of both of which are incorporated herein by reference.

Such steroids and combinations comprising one or more steroids will typically be combined in the compositions of the present invention at concentrations of between about 0.1 and 4.0 percent by weight (wt. %). The following steroids are preferred: dexamethasone, prednisolone and fluorometholone. The preferred steroids can be used at concentrations between about 0.125 and 1.0 wt. %.

Growth factors are agents which cause cells to migrate, differentiate, transform or mature and divide. They are polypeptides which can usually be isolated from many different normal and malignant mammalian cell types. Some growth factors can be produced by genetically engineered microorganisms, such as bacteria (*E. coli*) and yeasts; see, for example, Chapters 10 and 11 of *The Molecular and Cellular Biology of Wound Repair* (1986), the entire contents of the book of which are incorporated in the present specification by reference. Growth factors are known for their involvement in a variety of phenomena as set forth above. For example, epidermal growth factor (EGF) is known to stimulate the proliferation of epidermal and other epithelial tissues; see Barrandon et al., *Cell*, Vol. 50, 1131–1137 (Sep. 25, 1987) incorporated herein by reference. Both EGF and transforming growth factor (TGF), which has the same sequence homology as EGF and binds to the same cell surface receptor as EGF, have been suggested for use in wound healing, Id.; European Patent 190 018 (disclosing the use of TGF for the treatment of epithelial and stromal wounds); PCT WO 86/02271 (disclosing the use of human epidermal growth factor (hEGF) for treating epithelial and stromal wounds); and European Patent 140 998 (disclosing ophthalmic preparations containing hEGF for the treatment of keratitis, corneal erosion, corneal infiltration and corneal ulcers).

Growth factors which can be used according to the present invention include: EGF, fibroblast growth factor (FGF), insulin-like growth factor (IGF), platelet derived growth factor (PDGF), alpha and beta transforming growth factors ($TGF_A$ and $TGF_B$) and nerve growth factor (NGF). In addition, cell enhancing solutions which contain growth factors can be used, such as SGF-7, available from Scott Laboratories, Inc., and ITS, available from Collaborative Research Incorporated. Growth factors will typically be contained in the compositions of the present invention at concentrations between about 0.01 nanograms per milliliter (ng/ml) and 100 micrograms per milliliter (ug/ml). For example, EGF can be used at concentrations between about 500 ng/ml and 100 ug/ml, preferably between about 10 ug/ml and 50 ug/ml; and FGF can be used from between about 1.0 ng/ml and 50 ug/ml, preferably at about 10 ug/ml. In addition TGF can be used at concentrations of at least about 100 ng/ml; see Lawrence et al., *Annal. Surg.* 203, pp. 142–147 (1986).

Basement membrane components can be used to prevent or alleviate scar formation due to improper collagen repair. It has been theorized that basement membrane components promote wound healing by contributing to the reformation of destroyed basement membranes or functioning as a basement membrane, thereby providing a surface across which epithelial cells can migrate and allowing re-epithelialization of the cornea to progress; see Fujikawa, et al., *Fibronectin in Healing Rabbit Corneal Wounds*, Laboratory Investigation, Vol. 45, No. 2, pp. 120–8 (1981) incorporated herein by reference. Basement membranes are thin amporphous, sheetlike structures which separate certain parenchymal cell types, endothelium and epithelium, from connective tissue stroma. For a discussion of basement membranes and their role in wound repair; see *The Molecular and Cellular Biology of Wound Repair*, Chapter 22, specifically p. 550 (1986).

In the present invention, basement membrane components are employed to encourage and aid corneal epithelial cells in division, migration and sticking. They influence endothelial cells by providing an attachment and organizational foundation for the endothelial cells. They also help with the organization of collagen in the stroma. Basement membrane components which can be used to prevent corneal haze resulting from improper collagen repair include: heparin; heparin sulfate; fibronectin; laminin; connective tissue activating peptides such as vinculin; gelatin; glycosaminoglycans; and various types of collagen, especially type IV collagen. The present compositions will typically contain one or more basement membrane components at concentrations between about 0.01 ng/ml and 1 milligram per milliliter (mg/ml), preferably about 1 ug/ml.

Regulators of collagen structure can also be used as wound healing modulators to control or prevent scar formation due to improper collagen repair. As used herein "regulators of collagen structure" are wound healing modulators which degrade or inhibit the breakdown of collagen in the stroma or the collagen released by dead or injured cells; see *The Molecular and Cellular Biology of Wound Repair*, at pp. 224–226. These regulators can act in two ways, to degrade damaged connective tissue, such as collagen at inflammatory sites, or to act in the reverse manner inhibiting the degradation of connective tissue. Regulators of collagen structure which can be used to degrade collagen include, for example: collagenases, elastases, proteases and proline hydroxelase. Regulators of collagen structure which will inhibit the degradation of collagen include all known inhibitors of the aforementioned enzymes including phenylmethylsulfonyl fluoride (PMSF) and pyrridine-dicarboxylic acid esters used as proline hydroxylase inhibitors, fibrosuppressants and immunosuppressants as disclosed in U.S. Pat. No. 4,717,727, the contents of which are hereby incorporated by reference in this specification. Regulators of collagen structure can be used at concentrations of between about 10 ug/ml to about 10 mg/ml.

To prevent or reduce scar formation due to improper epithelial cell coverage of the cornea after photoablation, various wound healing modulators can be used. Prior to, or during, photoablation of the anterior surface of the cornea the epithelial cells are removed. Therefore, after surgery it is necessary for re-epithelialization to occur. Improper epithelial cell coverage leading to scar formation may be prevented or alleviated through the use of wound healing modulators including growth factors such as EGF, IGF, PDGF, FGF, $TGF_B$, $TGF_A$ and NGF and basement membrane components. These wound healing modulators can be used at concentrations previously discussed.

In addition, aldose reductase inhibitors (ARIs) can be used as wound healing modulators according to the present invention. For example, ARIs, such as those disclosed in U.S. Pat. Nos. 4,717,725, 4,600,717, 4,436,745, and 4,438,272, 1988, the entire contents of which are incorporated herein by reference, can be used to help prevent corneal haze from developing due to improper epithelial cell coverage. These compounds inhibit the enzyme aldose reductase. The enzyme's inhibition appears to be related to the mechanism of wound healing in the diabetic individual; see Ohasti et al., *Aldose Reductase Inhibitor (CT-*112) *Eyedrops for Diabetic Corneal Epitheliopathy*, American Journal of Ophthalmology, Vol. 105, No. 3 (March, 1988). ARIs can be used at concentrations between about 0.1 wt. % and 2.0 wt. %.

Concerning corneal haze formation resulting from scar formation attributable to inflammation, the following wound healing modulators can be used in accordance with the foregoing discussion: steroids; growth factors such as EGF, FGF, IGF, PDGF, TGF, TGF and NGF, and aldose reductase inhibitors. Additionally, nonsteroidal antiinflammatory agents (NSAIs) can be used as wound healing modulators to prevent or control corneal haze resulting from UV photoablation. Nonsteroidal antiinflammatory agents which can be used according to the present invention will typically comprise: loxoprofen, as disclosed in British Patent No. GB 2,144,993A, published Mar. 12, 1985, incorporated herein by reference. Compounds disclosed in U.S. Pat. No. 4,559,343, issued Dec. 17, 1985 and incorporated herein by reference can also be used. Those compounds include: flurbiprofen; suprofen; aryl or heteroaryl-carboxylic acids such as mefenamic acid, flufenamic acid, clonixin, flufenisal; aryl or heteroarylalkynoic acids such as 4-(t-butyl) benzeneacetic acid, ibufenac, ibuprofen, alkylofenac, fenoprofen, naproxen, indomethacin, tolmetin, ketoprofen and namoxyrate. Additionally, ketorolac, or pyrrolo pyrroles, disclosed in U.S. Pat. No. 4,454,151 issued Jun. 12, 1984 and incorporated herein by reference, can be used. Such NSAIs can be used at concentrations of between about 0.1 and 2.0 wt. %. Preferred NSAIs include: suprofen, loxoprofen, flurbiprofen, indomethacin and ketorolac. These compounds are typically present in the compositions at the following concentrations: suprofen at about 1.0 wt. %, loxoprofen at about 1.0 wt. %, flurbiprofen at about 0.25 wt. %, indomethacin from about 0.1 to 1.0 wt. % and ketorolac at about 0.5 to 1.0 wt. %.

Anti-oxidants can also be used as wound healing modulators to control or prevent scar formation resulting from inflammation following photoablation of the cornea. When tissue, such as the cornea, is subjected to trauma, for example laser radiation, reactive species in excess of those normally present as a result of enzymatic and nonenzymatic reactions are produced. These reactive species, including free radicals, can cause tissue damage; see *The Molecular and Cellular Biology of Wound Repair*, specifically Chapters 1, 6 and 7; and Fisher, *Intracellular Production of Oxygen Derived Free Radicals*, Oxygen Radicals and Tissue Injury, Proceedings of a Book Lodge Symposium (April 1987), which is incorporated herein by reference. Anti-oxidants prevent scar formation by scavenging free radicals. Suitable anti-oxidants include, for example: ascorbic acid; glutathione; see Meister, *Selective Modification of Glutathione Metabolism*, Science, Vol. 220 (April, 1988); alpha tocopherol; and selenous acid or sodium selenate. Such anti-oxidants can be used at concentrations between about 0.001 ng/ml and 1 mg/ml, preferably about 100 ng/ml.

Immunomodulators can also be used to control inflammation which may contribute to the appearance of corneal haze. Immunomodulators which may be used include: cyclosporin A and cyclosporin G, leflunomide, N-(4-trifluoromethylphenyl)-N-(2-cyano-1-hydroxy-1-propen-1-yl)carboxamide and interferon (δ,β and α). Immunomodulators can be used at concentrations between about 2 and 10 wt. %.

Antiallergics are wound healing modulators which can also be used to prevent corneal haze resulting from scar formation due to inflammation. This class of compounds includes for example: cyproheptadine, diphenriamine, azelastine, cimetidine, neodocromil, cromolyn, lodoxamide, pheniramine and 6-methyl-N-(1H-tetrazol-5yl)-z-pyridinecarboxamide. Such antiallergic compounds can be used at concentrations of about 0.1 to 4.0 wt. %.

As indicated above, a second possible explanation for the development of corneal haze resulting from photoablation of the cornea is that the fibroblasts of the stroma may be improperly activated in response to the laser irradiation. As a result the fibroblasts aberrantly metabolize cellular components, such as extracellular matrix proteins in an unhealthy, unorganized fashion. These components appear as specks in the stroma observable as a granular corneal haze.

Wound healing modulators which can be used to prevent or alleviate corneal haze resulting from improperly activated fibroblasts include: growth factors, such as EGF, FGF, $TGF_A$, $TGF_B$, NGF, PDGF, insulin like growth factor (IGF) and insulin; and tumor necrosis factor (TNF). Such growth factors can be used in accordance with the foregoing discussion of this class of wound healing modulators. In addition, the immunomodulators, antiallergics and basement membrane components, as previously set forth, can be used in this situation.

A third possible explanation for the appearance of corneal haze following photoablation of the cornea involves radiation damage of collagen fibrils resulting in improper alignment within the stroma. The clear character of the cornea is in part dependent on the proper configuration and spacing of the collagen fibrils within the stroma. Therefore, improper alignment may appear as specks or haze in the stroma.

Wound healing modulators which can be used to prevent or alleviate the formation of corneal haze due to damage to collagen fibrils include: the growth factors TNF, EGF, FGF, IGF and insulin; steroids; immunomodulators, basement membrane components and antioxidants, all of which may be used as previously discussed.

A fourth possible explanation for the formation of corneal haze is that the laser may kill or damage fibroblasts in the stroma. A dead fibroblast will cease functioning relative to proper formation of the collagen matrix and can also act as a refractive object until absorbed. If the fibroblast is damaged, but not killed by the laser, it could continue functioning but possibly in a faulty manner due to DNA damage. For example, fibroblasts make a procollagen molecule that could be improperly enzymatically clipped resulting in secretion of defective collagen.

Wound healing modulators which can be used to combat corneal haze resulting from dead or damaged fibroblasts include the growth factors EGF, FGF, PDGF, $TGF_A$, $TGF_B$ and NGF, all of which may be used as previously discussed. In addition, fatty acid derivatives, which are products of the arachidonic acid cascade such as cyclo-oxygenase products (prostaglandins and thromboxanes which down regulate) and leukotrienes ($LTB_4$ and $LTC_4$ which up regulate) can contribute to the treatment of corneal haze by stimulating polymorphonuclear leukocytes (PMN), macrophages and fibroblasts, thereby increasing clearance of the corneal haze. For a discussion regarding the regulation of macrophage-derived fibroblast growth factor, which is involved in wound healing and scar formation, by arachidonate metabolites, see *Journal of Leukocyte Biology* 42:106–113(1987), the contents of which are incorporated herein by reference. Immunomodulators can also be used in this situation to control the activity of lymphocytes, which can contribute to the prevention and treatment of corneal haze in accordance with the foregoing discussion of this class of compounds.

A fifth possible cause of the corneal haze is the corneal edema which may occur following photoablation. Wound healing modulators which can be used to combat the formation of and treat corneal haze attributable to edema include: growth factors such as EGF, FGF, $TGF_A$ $TGF_B$ and NGF; steroids; nonsteroidal antiinflammatories; antiallergics; anti-oxidants and aldose reductase inhibitors. Additionally antimicrobial compounds, discussed below, can be particularly useful in treating corneal haze attributable to edema.

Photoablation leaves the cornea denuded of its protective epithelial layer leaving it prone to infection. Antimicrobials can be used according to the present invention pre-operatively and post-operatively thereby safeguarding against corneal infection which inhibits healing, possibly leading to corneal edema and the formation of corneal haze. Antimicrobials which can be used according to the present invention include: chloramphenicol, erythromycin, gentamycin, polymyxin, sulfacetamide, tetracycline, tobramycin, sulfisoxazole, diolamine, ciprofloxacin, natamycin, neomycin, ofloxacin, norfloxacin, trifluorothymidine, acyclovir, gancyclovir, vancomycin and other antibacterial, antiviral and antifungal agents. The compositions comprise one or more antimicrobials or combinations of antimicrobials and other wound healing modulators. Such antimicrobials are used at concentrations between about 0.05 and 3.0 wt. %. preferably less than about 1.0 wt. %.

As set forth above, it is believed corneal haze resulting from laser irradiation is related to one or more of the following: wound repair; improperly activated fibroblasts; damaged collagen fibrils; damaged or dead fibroblasts in the stroma; and corneal edema. Corneal haze may be prevented with varying degrees of success with steroids, growth factors, basement membrane components, regulators of collagen structure, aldose reductase inhibitors, NSAIs, antioxidants, immunomodulators and antiallergics (which are particularly effective against corneal haze resulting from wound repair); growth factors, immunomodulators, antiallergics and basement membrane components (which are particularly effective when fibroblasts of the stroma have been improperly activated); growth factors, steroids, immunomodulators, basement membrane components and anti-oxidants (which are particularly effective in alleviating the formation of corneal haze due to damaged collagen fibrils); growth factors and fatty acid derivatives of the arachidonic acid cascade (which are particularly effective when damaged or dead fibroblasts are present); and growth factors, steroids, NSAIs, antiallergics, anti-oxidants, aldose reductase inhibitors and antimicrobials (which are particularly effective in treating corneal haze attributable to edema).

The wound healing modulators of the present invention can be applied alone or in combination with other wound healing modulators. In addition, individual wound healing modulators or combinations thereof can be applied uniquely or sequentially. While the effective dose and treatment regime are left to the discretion of the clinician, the following procedures are recommended.

The wound healing modulators which can be used to prevent or alleviate corneal haze are formulated in compositions for topical application to the eye. As will be appreciated by those skilled in the art, the compositions can be formulated in various pharmaceutically acceptable forms for topical ophthalmic delivery including: solutions, suspensions, emulsions, gels and solid inserts, depending on the nature and characteristics of the wound healing modulators. Preferred formulations are aqueous solutions. In addition, the wound healing modulators of the present invention can be applied via the use of a collagen shield, contact lens or other solid matrix placed on the ocular surface. Such shields, lenses or matrices can provide for slow release of the modulators as well as serving as a protective environmental barrier.

In addition to the principal active ingredients, the wound healing modulator compositions of the present invention may further comprise various formulatory ingredients, such as antimicrobial preservatives and tonicity agents. For example, antimicrobial preservatives include: benzalkonium chloride, thimerosal, chlorobutanol, methylparaben, propylparaben, phenylethyl alcohol, EDTA, sorbic acid, POLYQUAD and other agents equally well known to those skilled in the art. Such preservatives, if employed, will typically be used in an amount from about 0.0001 wt. % to 1.0 wt. %. Suitable agents which may be used to adjust tonicity or osmolality of the compositions include: sodium chloride, potassium chloride, mannitol, dextrose glycerine and propylene glycol. If used, such agents will be employed in an amount of about 0.1 wt. % to 10.0 wt. %. However, preferable compositions of the present invention will not include preservatives or tonicity agents which are known to adversely affect or irritate the eye, particularly the cornea.

As will be understood by those skilled in the art, the administration, sequence of administration when more than one wound healing modulator is used, and the concentrations of the wound healing modulators used depends on numerous factors. These factors can include: the specific wound healing modulator or modulators being used, the nature of the surgical procedure, and various clinical factors, including the extent and type of haze being treated, the medical history of the patient, symptoms apparent prior to, during, or after surgery, such as inflammation or edema, etc. Selection of specific wound healing modulators or combinations thereof, their concentrations and sequence of delivery to the eye will be made by the skilled clinician guided by the foregoing description.

Regardless of the reason or combination of reasons for development of corneal haze, there are compounds, or compositions, collectively referred to herein as "adjuncts" which can be used alone, or in addition to the wound healing modulators discussed above, that contribute to the overall health and comfort of the eye, thus contributing to the prevention of corneal haze and its treatment.

For example, during and following photoablation of the cornea, elevation of intraocular pressure may occur. Control of intraocular pressure contributes to the health of the cornea thereby allowing the cornea to heal without resulting corneal haze. Adjuncts for controlling intraocular pressure which can be used in combination with wound healing modulators include antihypertensive agents. Antihypertensive agents which can be used include, for example; timolol, betaxolol, levobunalol, glycerin, isosorbide, manitol, urea, paraminoclonidines, epinephrine and carbonic anhydrase inhibitors. The compounds can be topically applied to the eye following photoablation at concentrations between about 0.1 and 2.0 wt. % preferably about 0.5 wt. %. In addition, miotics can be used to control intraocular pressure. For example miotics such as carbachol, pilocarpine, physostigmine, echothiophate and isofluorphate can be used.

Humectants may be used prior to, during and after photoablation of the cornea. These adjuncts promote healing of the cornea by providing lubrication and preserving the natural tear physiology. Humectants can include preparations which typically comprise hydroxyethylcellulose, hydroxypropylcellulose, hydroxypropylmethylcellulose, methylcellulose, polyvinyl alcohol, cellulose esters, povidone or other suitable polymeric systems.

Epithelial cell health promoters as used herein, are compounds known to contribute to the health of the epithelial cells of the cornea. The presence of these compounds prior to, during, and/or after photoablation of the cornea can contribute to the prevention of corneal haze by encouraging the rapid resumption of epithelial integrity and prevention of stromal edema. Epithelial cell health promoters which can be used as adjuncts to the wound healing modulators of the present invention can include: ascorbic acid; retinoids, such as retinoic acid, retinol, retinal and retinoyl B-glucuronide; aloe vera; collagenase inhibitors; prostaglandins, such as prostaglandin E and elastase inhibitors.

The present invention also encompasses methods of treatment of an eye exposed to laser radiation during ophthalmic procedures. Methods of treatment, during ophthalmic surgery, with compositions containing wound healing modulators, as disclosed above, include application of the compositions before laser exposure, during the procedures, for example when the eye is moistened and a wet keratoscope reading is taken during corneal sculpting using a laser and/or immediately after irradiation. In addition, and as previously discussed, the compositions of the present invention can be applied uniquely or when the use of more than one wound healing modulator is indicated, the medicaments can be administered sequentially.

The following formulation is an example of a wound healing modulator composition that can be used for the prevention and treatment of corneal haze resulting from laser irradiation. It is not limiting but considered representative of useful compositions of the present invention.

Example:

The following composition can be formulated by mixing the specific components at the indicated concentrations. The compositions should be either prepared under sterile conditions or sterilized after their preparation and prior to their use.

Example 1 (Suspension)

| Component | Concentration |
| --- | --- |
| Dexamethasone | 0.1 wt. % |
| Neomycin Sulfate | Equivalent to Neomycin 3.5 mg/ml |
| Polymixin Sulfate | 10,000 units/ml |
| Benzalkonium Chloride | 0.0004 wt. % |
| Hydroxypropyl Methylcellulose | 0.5 wt. % |
| Purified Water | q.s. |

We claim:

1. A method of treating a cornea prior to, during or after laser irradiation and resulting photoablation and volumetric removal of corneal tissue, comprising: applying to the affected cornea a composition containing an antiinflammatory amount of a steroid, an antimicrobial and a pharmaceutically acceptable carrier therefor.

2. The method of claim 1 wherein the steroid comprises dexamethasone.

3. The method of claim 1 wherein the steriod comprises fluorometholone.

4. The method of claim 1 wherein the steroid comprises rimexolone.

5. The method of claim 1 wherein the steroid comprises prednisolone.

6. The method of claim 1 wherein the steroid comprises prednisone.

7. The method of claim 1 wherein the steroid comprises medrysone.

8. The method of claim 1 wherein the steroid comprises betamethasone.

9. The method of claim 1 wherein the steroid comprises triamcinolone.

10. The method of claim 1 wherein the steroid comprises hydrocortisone.

11. The method of claim 1 wherein the antimicrobial comprises tobramycin.

12. The method of claim 1 wherein the antimicrobial comprises ciprofloxacin.

13. The method of claim 1 wherein the steroid comprises dexamethasone and the antimicrobial comprises tobramycin.

* * * * *